United States Patent
Viertiö-Oja (10) Patent No.: US 9,398,863 B2
(45) Date of Patent: Jul. 26, 2016

(54) DETECTION OF ANOMALIES IN MEASUREMENT OF LEVEL OF HYPNOSIS

(75) Inventor: Hanna E. Viertiö-Oja, Espoo (FI)

(73) Assignee: General Electric Company, Schenectady, NY (US)

(*) Notice: Subject to any disclaimer, the term of this patent is extended or adjusted under 35 U.S.C. 154(b) by 1787 days.

(21) Appl. No.: 11/765,627

(22) Filed: Jun. 20, 2007

(65) Prior Publication Data

US 2008/0317672 A1    Dec. 25, 2008

(51) Int. Cl.
| | |
|---|---|
| *A61B 5/04* | (2006.01) |
| *A61B 5/0476* | (2006.01) |
| *A61B 5/00* | (2006.01) |
| *A61M 5/172* | (2006.01) |
| *A61M 16/00* | (2006.01) |
| *A61M 16/18* | (2006.01) |
| *G06F 19/00* | (2011.01) |
| *G09B 23/28* | (2006.01) |

(52) U.S. Cl.
CPC .............. *A61B 5/0476* (2013.01); *A61B 5/4035* (2013.01); *A61B 5/4821* (2013.01); *A61M 5/1723* (2013.01); *A61M 16/0051* (2013.01); *A61M 16/18* (2013.01); *G06F 19/3437* (2013.01); *G06F 19/3456* (2013.01); *G09B 23/28* (2013.01); *A61M 2205/3561* (2013.01); *A61M 2205/3584* (2013.01); *A61M 2205/502* (2013.01); *A61M 2205/52* (2013.01); *A61M 2230/04* (2013.01); *A61M 2230/10* (2013.01); *A61M 2230/30* (2013.01)

(58) Field of Classification Search
USPC ................................................. 600/544–545
See application file for complete search history.

(56) References Cited

U.S. PATENT DOCUMENTS

| | | | | |
|---|---|---|---|---|
| 5,775,330 A | * | 7/1998 | Kangas et al. ................. | 600/544 |
| 6,016,444 A | * | 1/2000 | John ............................. | 600/544 |

(Continued)

FOREIGN PATENT DOCUMENTS

WO    03/084396 A1    10/2003

OTHER PUBLICATIONS

Muthuswamy et al., The use of fuzzy integrals and bispectral analysis of the electroencephalogram to predict anesthesia, 1999, IEEE Transactions on Biomedical Engineering, vol. 46(3) pp. 291-299.*

(Continued)

*Primary Examiner* — Navin Natnithithadha
*Assistant Examiner* — Michael R Bloch
(74) *Attorney, Agent, or Firm* — Andrus Intellectual Property Law, LLP (57) ABSTRACT

The invention relates to detection of anomalies related to a measurement of the hypnotic level of a subject. In order to detect when a measure indicative of the hypnotic level of a subject is anomalous either due to a medical reason or due to an interference, the measure is monitored and state information indicative of the activity of the autonomous nervous system of the subject and drug effect information indicative of the hypnotic drug effect in the subject are employed to check whether the measure fulfills a predetermined consistency condition requiring that the measure changes consistently with at least one of the drug effect information and the state information. An anomaly, indicative of an abnormal change in the measure, is detected when the measure fails to fulfill the predetermined consistency condition.

23 Claims, 3 Drawing Sheets

(56) References Cited

U.S. PATENT DOCUMENTS

| | | |
|---|---|---|
| 6,631,291 B2 | 10/2003 | Viertiö-Oja et al. |
| 2002/0082513 A1* | 6/2002 | Ennen et al. ............... 600/544 |
| 2002/0173729 A1* | 11/2002 | Viertio-Oja et al. ......... 600/544 |
| 2003/0101076 A1* | 5/2003 | Zaleski ............... G06Q 50/22 705/2 |
| 2003/0156143 A1* | 8/2003 | Westenskow et al. ........ 345/848 |
| 2004/0015091 A1* | 1/2004 | Greenwald et al. ........... 600/513 |
| 2004/0082876 A1 | 4/2004 | Viertio-Oja et al. |
| 2005/0010116 A1* | 1/2005 | Korhonen et al. ........... 600/481 |
| 2006/0084882 A1* | 4/2006 | Skinner ....................... 600/515 |
| 2006/0217614 A1 | 9/2006 | Takala et al. |
| 2006/0217628 A1* | 9/2006 | Huiku ..................... A61B 5/02 600/544 |
| 2007/0208322 A1* | 9/2007 | Rantala et al. .............. 604/503 |

OTHER PUBLICATIONS

FR Search Report and Written Opinion issued in connection with corresponding FR Application No. 0854082 on Feb. 16, 2011.

* cited by examiner

DETECTION OF ANOMALIES IN MEASUREMENT OF LEVEL OF HYPNOSIS

FIELD OF THE INVENTION

The present invention relates generally to the monitoring of the cerebral state of a subject. More particularly, the present invention relates to the detection of anomalies in an EEG based measure indicative of the level of hypnosis of the subject. In this context, an anomaly refers to a situation in which the normal logical relation between measured hypnotic level and the drug effect in the brain is altered due to an abnormal reason. The invention finds a typical application in patient monitoring during anesthesia.

BACKGROUND OF THE INVENTION

Hypnosis is an artificially induced altered state of consciousness, which resembles sleep. In anesthesia, the level of hypnosis is controlled by induction of sedative drugs or anesthetic agents. Hypnosis always refers to the suppression or alteration of the (cortical) brain functions. The depth of hypnosis can be clinically tested by non-noxious stimulation of the patient, such as loud speak or light squeeze, shake or touch, and by observing the patient responses, such as eye opening, communication ability, etc. Hypnotic drugs typically increase the overall inhibitory neuronal functions, as they usually affect the GABA (gamma-aminobutyric acid) system in the brain. Therefore, the hypnotics suppress both the cortical and subcortical activities in the brain. As a consequence, also the autonomic and reflex functions in the brain are altered and suppressed.

The depth of hypnosis is not directly measurable. Therefore, drug delivery systems have to derive the level of hypnosis from a surrogate signal or from indirectly measured parameters. The most common and popular surrogate signal for this purpose is the EEG, from which several parameters may be determined. During the past few years, some commercial validated devices for measuring the level of hypnosis in clinical set-up during anesthesia or sedation have become available. Such devices, which are based on a processed EEG signal and examine the signal as a whole with its multiple features, are marketed, for example, by GE Healthcare Finland Oy, Kuortaneenkatu 2, FIN-00510 Helsinki (Entropy Index) and by Aspect Medical Systems, Inc., 141 Needham Street, Newton, Mass. 02464, U.S.A. (Bispectral Index, BIS™).

In particular situations, the relation between the measured hypnotic level of the patient and the hypnotic drug concentration in the brain may be abnormal. For example, if severe bleeding, a stroke, or cardiac arrest takes place, the level of hypnosis is no longer controlled only by the hypnotic drug but also by the oxygenation of the brain. Certain anesthetic agents, such as sevoflurane, tend to induce epileptic seizures, which affect the level of hypnosis and also have an effect on the EEG-based measurement. Due to an underlying illness, the patient may show an abnormal response to some of the administered drugs. In these situations, interpretation of the measurement requires particular expertise.

Another issue aggravating the assessment of the level of hypnosis is that the EEG signals to be measured are weak, of the order of a few hundred microvolts, which makes them vulnerable to both external interferences caused by surrounding equipment and internal interferences caused by patient's eye or body movements and/or interfering EMG or ECG signal components, for example. With regard to the external interferences, an operation room is an especially demanding environment, since it is equipped with a plurality of devices that may act as interference sources from the point of view of the assessment of the level of hypnosis. Modern artifact detection methods have helped to minimize the problem but not completely solved it.

It has also been suggested that the administration of a hypnotic drug could be controlled in a closed loop fashion. U.S. Pat. No. 6,631,291 B2 discloses a system in which a quantification of the complexity of the EEG signal data measured from the patient is used to determine the patient's hypnotic level and to control the administration of a hypnotic drug to the patient in a closed loop fashion. A closed loop drug administration system generally refers to a system in which the administration is controlled automatically based on feedback measurement data measured from the patient, whereas an open loop drug administration system refers to a system in which such feedback measurement data is not automatically utilized for the control of drug administration.

Furthermore, U.S. Patent Application 2006/0217628 discloses a closed loop system in which an index of hypnosis and an index of nociception are measured from the patient and supplied to a control unit. The control unit determines the location of patient state on a two-dimensional plot. The control unit further compares the determined location with the input parameters defining the targeted location and controls the anesthetic delivery system to shift the state towards the targeted state or to maintain the state of the patient in the targeted domain.

Due to the above-mentioned difficulties in recognizing all factors possibly disturbing the measurement of the level of hypnosis, the performance of the present-day measurement systems is compromised in presence of anomalies, i.e. in situations in which the logical relation between the measured hypnotic level and the drug effect in the brain is altered due to an abnormal reason. As discussed above, the anomalies may be of medical origin or caused by unwanted electrical signals (interference in the measurement).

The above-mentioned difficulty in recognizing all disturbing factors also complicates the design of a closed loop drug administration system. In anomalous situations the control system would often lack the pieces of information that would be necessary for the correct interpretation of the situation and for correct decisions regarding drug administration.

SUMMARY OF THE INVENTION

The present invention seeks to accomplish a novel mechanism for detecting anomalies in connection with a measurement of the level of hypnosis of a patient. The present invention further seeks to accomplish a mechanism that prevents such situations from degrading the reliability of systems or applications in which decisions are made based on the level of hypnosis, such as drug administration systems. The present invention rests on the discovery that during anesthesia the level of hypnosis normally depends only on the hypnotic component of the anesthetic drug effect and on the surgical stimulation which may cause lightening of hypnosis via an arousal reaction. Any change observed in an EEG based measure should thus be logically traceable to either a consistent change in the administered drug levels or to an autonomic arousal response of the subject. If a change in the measure cannot be related to either of these causes, it is highly likely that the change is due to an anomaly, such as those discussed above.

Consequently, in order to detect anomalies in the measurement of the level of hypnosis, the invention utilizes drug effect information indicative of the hypnotic drug effect in the subject and state information indicative of the activity of the autonomous nervous system (ANS) of the subject.

If consistency is not found between a change in the measured hypnotic level and a change in at least one of the drug effect information and the state information, an anomaly is detected and appropriate actions are taken. For example, if neither the drug effect information nor the state information is able to explain a change in the hypnotic level, i.e. if a consistent change is present in neither the state information nor the drug effect information, an anomaly is detected. A consistent change here refers to a change that is substantially concurrent with a change in the hypnotic level and logical in the sense that it occurs in the correct direction with respect to the change in the hypnotic level. As discussed below, the detection of anomalies may be based on absence of consistency in both the state and drug effect information or presence of inconsistency in at least one of the state and drug effect information.

Thus one aspect of the invention is providing a method for detecting anomalies in a measurement of the hypnotic level of a subject. The method includes monitoring a measure indicative of the hypnotic level in the subject, receiving state information indicative of the activity of the autonomous nervous system of the subject, and receiving drug effect information indicative of the hypnotic drug effect in the subject. The method further includes checking whether the measure fulfills a predetermined consistency condition requiring that the measure changes consistently with at least one of the drug effect information and the state information and detecting an anomaly when the measure fails to fulfill the predetermined consistency condition, wherein the anomaly is indicative of an abnormal change in the measure.

Another aspect of the invention is that of providing an apparatus for detecting anomalies in a measurement of the hypnotic level of a subject. The apparatus includes a monitoring unit configured to monitor a measure indicative of the hypnotic level in the subject, a first interface unit configured to receive state information indicative of the activity of the autonomous nervous system of the subject, and a second interface unit configured to receive drug effect information indicative of the hypnotic drug effect in the subject. The apparatus further includes a calculation unit configured (i) to perform a consistency check based on the drug effect information and the state information, thereby to check whether the measure fulfills a predetermined consistency condition requiring that the measure changes consistently with at least one of the drug effect information and the state information and (ii) to detect an anomaly when the measure fails to fulfill the predetermined consistency condition, wherein the anomaly is indicative of an abnormal change in the measure.

A further aspect of the invention is that of providing a computer program product for detecting anomalies in a measurement of the hypnotic level of a subject. The program product includes a first program code portion configured to perform a consistency check based on drug effect information indicative of hypnotic drug effect in the subject and state information indicative of the activity of the autonomous nervous system of the subject, thereby to check whether a measure indicative of the hypnotic level of the subject fulfills a predetermined consistency condition requiring that the measure changes consistently with at least one of the drug effect information and the state information, and a second program code portion configured to detect an anomaly when the measure fails to fulfill the predetermined consistency condition, wherein the anomaly is indicative of an abnormal change in the measure.

The present invention enables the physicians to be alerted to the presence of an anomaly. The present invention further enables safer application of the level of hypnosis in various control and decision support applications, such as closed loop drug administration systems, since the periods can be efficiently detected, during which anomalies have an effect on the measure of hypnotic level.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 6 in the appended drawings, wherein.

DETAILED DESCRIPTION OF THE INVENTION

Figure 1:
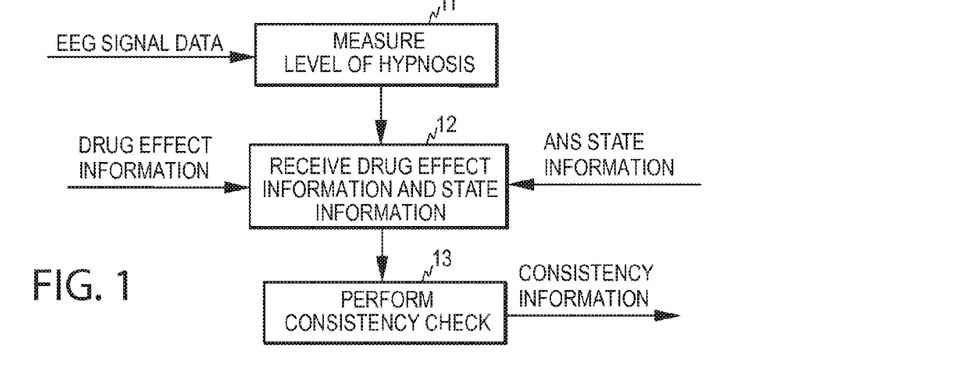
FIG. 1 is a flow diagram illustrating the general principle of the present invention.

FIG. 1 illustrates the detection mechanism of the invention. The mechanism detects anomalous situations in which the EEG based measure indicative of the level of hypnosis of a subject does not, due to an exceptional medical situation and/or measurement artifacts, fulfill a certain consistency condition that requires consistency between a change in the measured level of hypnosis and the change in at least one of the hypnotic drug effect and the ANS activity.

The EEG based measure of the hypnotic level is determined in a known manner based on one or more EEG signals obtained from the subject, step 11. The measure may be, for example, the above-described Bispectral Index by Aspect Medical or the Entropy Index by GE Healthcare. The Entropy Index is an example of a measurement belonging to a group of techniques utilizing a measure of the complexity of EEG signal data as an indication of the hypnotic level. Since the core of the present invention does not relate to the determination of the hypnotic level, it is not discussed in detail in this context. Reference is made to the above-mentioned U.S. Pat. No. 6,631,291 B2, which discusses various techniques for measuring the hypnotic level.

A consistency check is performed by comparing the value of the measure with two types of information available in the system or generated for this purpose: drug effect information and ANS state information (steps 12 and 13). The drug effect information is indicative of the hypnotic drug effect in the subject, while the ANS state information is indicative of the activity of the autonomous nervous system of the subject. If the two types of information indicate that the measure of the hypnotic level does not meet a certain consistency criterion defined for the consistency check, the situation is considered as an anomaly. Generally, the consistency check examines, whether at least one of the drug effect information and the ANS state information changes consistently with the measure of the hypnotic level. If this is the case, the measure of the hypnotic level is regarded as consistent, otherwise an anomaly is detected. In different embodiments, the fulfillment of the consistency criterion may involve that consistency is to be found in either or both types of information, where the consistency of the respective information type is evaluated against changes in the measured level of hypnosis. Therefore, in different embodiments of the invention, an anomaly may be detected based on the absence of consistency in both the ANS state information and the drug effect information or on the presence of inconsistency in at least one of the ANS state information and the drug effect information.

Based on the check of consistency, consistency information is produced that indicates when the measure of the hypnotic level is anomalous. The consistency information may be produced continuously or only when an anomaly is detected.

Figure 2:
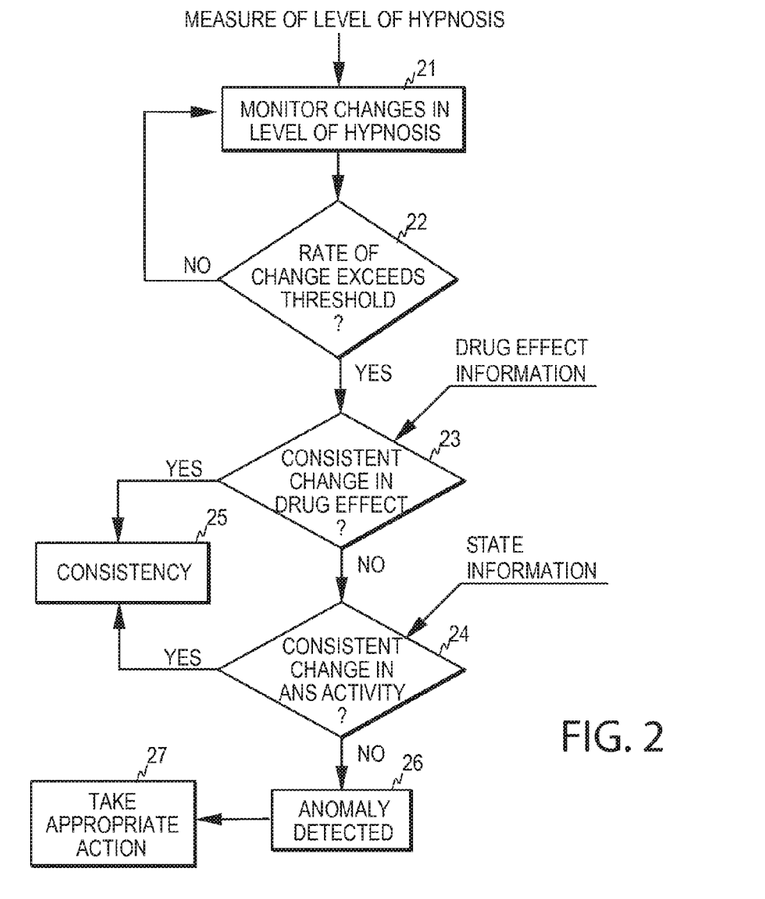
FIG. 2 is a flow diagram illustrating one embodiment of the invention in which a significant change in the level of hypnosis triggers a check procedure that examines whether the change of the hypnotic level is consistent with the information of the drug effect or with the information of the state of the autonomic nervous system.

FIG. 2 illustrates one embodiment of the invention for detecting when the measure of the hypnotic level is affected by an anomaly. Changes occurring in the measure are monitored (step 21). If it is detected at step 22 that the rate of change in the measure exceeds a certain threshold, the process first examines, whether the drug effect information indicates a consistent change in the hypnotic drug effect of the subject (step 23). If this is the case, the change in hypnotic level indicated by the measure is considered to be explained and the measure is regarded as consistent (step 25). If the measure is regarding as consistent (step 25), the checking may be aborted. However, if the drug effect information does not indicate a consistent change in the hypnotic drug effect, the process examines whether the state information indicates a consistent change in the ANS activity of the subject (step 24). If a consistent change is found in the ANS activity, the hypnotic level indicated by the measure is considered to be explained, i.e. the change in the measure is regarded to be caused by simultaneous surgical stimulation. However, if the state information does not indicate a consistent change in the ANS activity, the situation is regarded as anomalous (step 26) and appropriate action is taken (step 27).

The drug effect information may be obtained from an associated pharmacokinetic model. Generally, a pharmacokinetic model describes how the drug is distributed in the course of time from the site of delivery to different parts of the body and to the particular organ, such as the brain, in which the drug is supposed to have its effect. A pharmacokinetic model comprises of a set of mathematical differential equations that describes the distribution of a drug within the body as a function of time. The model includes both drug-specific and patient-specific parameters. The drug-specific parameters describe the diffusion and solubility properties of the drug, whereas the patient-specific parameters describe the properties of the patient that affect the drug distribution, such as weight, height, age, and gender. The body of the patient is represented by a simplified system of typically four tissue compartments among which the drug is distributed according to the differential equations.

The drug effect can be assumed to be approximately proportional to the drug concentration, or its relation to the concentration can be estimated more precisely by means of a pharmacodynamic model. A pharmacodynamic model defines the effect of the drug as a function of its concentration at the site at which it is effective, i.e. effect-site concentration. Such models may also use anthropometric data. For hypnotic drugs the effect is the hypnotic state of the patient, whereas and the effect-site is the brain.

Consequently, since the pharmacokinetic/pharmacodynamic models indicate the effect in the brain of the hypnotic drug administered, they may be used at step 23 to check whether a change in the hypnotic level is caused by a substantially simultaneous change in the concentration of a hypnotic drug in the brain. For example, if the level of hypnosis is measured as entropy values, an increase in the entropy values should be accompanied by a decrease in the drug effect, and vice versa. If it is detected at step 22 that the rate of change of the entropy exceeds a predetermined threshold, the process may check whether the effect of the hypnotic drug administered, as obtained from the pharmacoki-netic/pharmocodynamic models, has changed consistently. Pharmacokinetic and pharmacodynamic models are not, however, necessary for the invention. It is also possible that the process simply checks if there has been a recent change in the administration rate of the drugs that is consistent with the subsequent entropy change. For example, if a typical entropy scale from 0 to 100 is used for the measure of the hypnotic level and if the rate of change of the entropy exceeds 5 units per minute, the process may check whether the concentration of the hypnotic drug administered has changed recently by at least K micrograms per one kilogram of patient weight in the correct direction, wherein the value of K depends on the drug.

The state information, i.e. an indicator of the ANS activity, may be obtained in a known manner. Various mechanisms have been suggested to determine a measure indicative of ANS activation. One mechanism is disclosed in U.S. Patent Application 2006/0217614, which relates to a mechanism for determining an index of nociception for a subject. The said mechanism rests on the physiological fact that during periods of stress or pain, the activity of the sympathetic nervous system increases and becomes dominant, while the activity of the parasympathetic nervous system decreases. The index of nociception obtained is thus indicative of the ANS activation of the subject. As discussed in the said document, the content of which is incorporated by reference herein, at least a physiological signal indicative of the function of the cardiovascular system of the subject is used for determining the index. Such a signal may be a plethysmographic signal (PG), such as a photoplethysmographic (PPG) signal, a blood pressure (BP) signal, an ECG signal, or a Laser Doppler flow signal in peripheral tissues. Typically, however, the index of nociception is calculated based on a plethysmographic signal and an ECG signal.

Another automated mechanism for quantifying pain and stress during anesthesia or sedation is disclosed in WO 03/084396. This mechanism employs Pulse Wave Velocity (PWV) and Pulse Transit Time (PTT) to obtain an indication of the sympathetic activity of the subject. PWV is the velocity of the wave front propagating along an arterial tree by a bolus of blood ejected from a ventricle, while PTT is the time for the wave front to travel a fixed distance. During periods of increased sympathetic activity PWV increases and PTT decreases. If PTT is used as the state information indicative of the activity of the autonomous nervous system, ECG and PG signals are required from the subject for the determination of PTT.

Generally, an increase in the entropy values should be accompanied by an increase in the ANS activity. At step 24, the consistency between a change in the hypnotic level and in the state information may be determined, for example, by calculating the correlation between the entropy and the index of nociception. If the correlation is above a certain limit, the changes are regarded as consistent.

Figure 3:
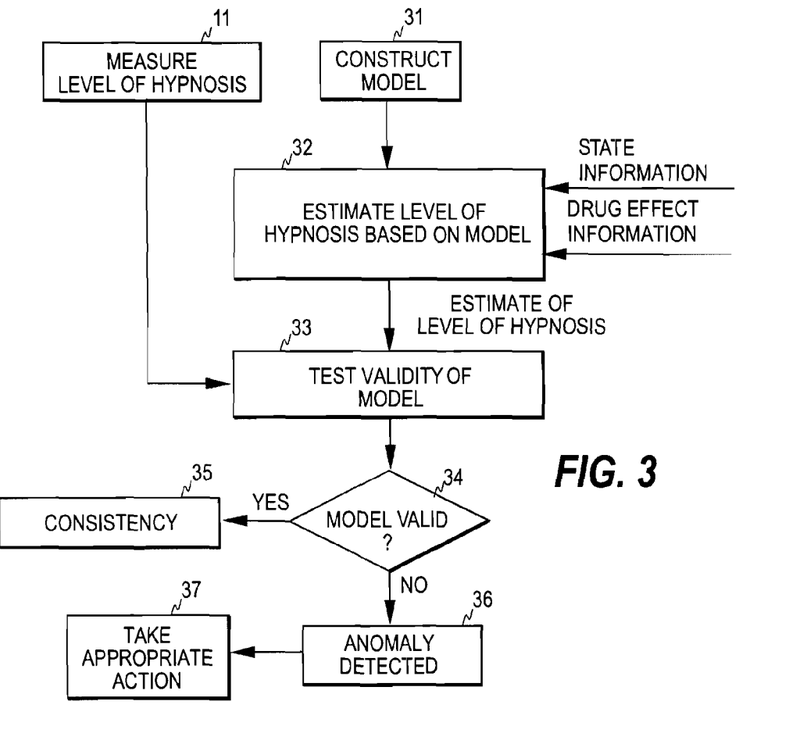
FIG. 3 illustrates a further embodiment of the invention in which the consistency of the measure of the hypnotic level is examined continuously.

FIG. 3 illustrates a further embodiment for detecting an anomaly. This embodiment is based on an internal model constructed in advance (step 31). The model is employed to produce an estimate for the level of hypnosis. The estimate is calculated based on the model, the drug effect information, and the state information (step 32). The validity of the model is then tested (step 33) by calculating, for example, the absolute value of the difference between the measured entropy value obtained from step 11 and the estimate of the entropy value. The measured entropy value is in agreement with the model, i.e. the model is valid, if the absolute value remains below a predetermined threshold value (steps 34 and 35). If the absolute difference exceeds the threshold value, i.e. if the measured entropy value deviates significantly from the value estimated by the model, the process decides that an anomaly is present (step 36), and appropriate action may be taken. In the embodiment of FIG. 3 the consistency check is performed continuously, whereas in the embodiment of FIG. 2 the check is carried out only when a significant change is detected in the measure indicative of the hypnotic level.

Figure 4:
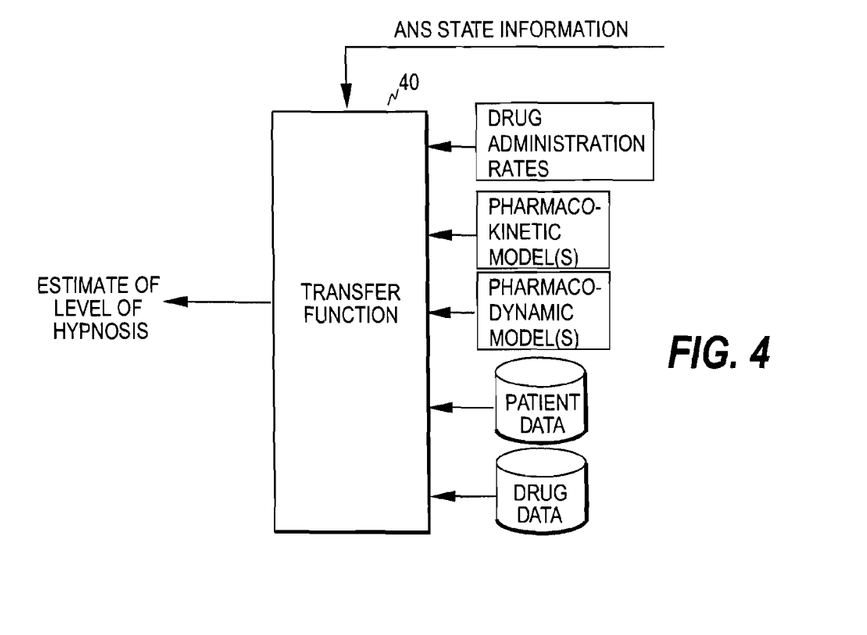
FIG. 4 illustrates an example of the estimation of the level of hypnosis in the embodiment of FIG. 3.

FIG. 4 illustrates an example of the estimation of the hypnotic level performed in steps 31 and 32 of FIG. 3. The model may estimate the hypnotic level, such as the entropy values, based on a predetermined transfer function 40 that may utilize various input data to produce an estimate of the hypnotic level. The input data used by the transfer function may include drug administration rates, pharmacokinetic/dynamic models, patient data (such as weight, height, and age), and drug data (such as the parameter values for the pharmacokinetic/dynamic models), which may be used to produce the drug effect information. The input data may further include the measured ANS state of the patient. Based on the input data and its internal rules and/or procedures, the transfer function produces an output signal that represents an estimate of the entropy value. The estimate is then compared with the measured value to detect the presence of an anomaly. The transfer function is such that the estimate changes logically (consistently) according to the changes indicated by the drug effect information and the state information. Consequently, the difference between the measure and the estimate stays within a predetermined value range as long as there is no abnormal change in the measured entropy.

Figure 5:
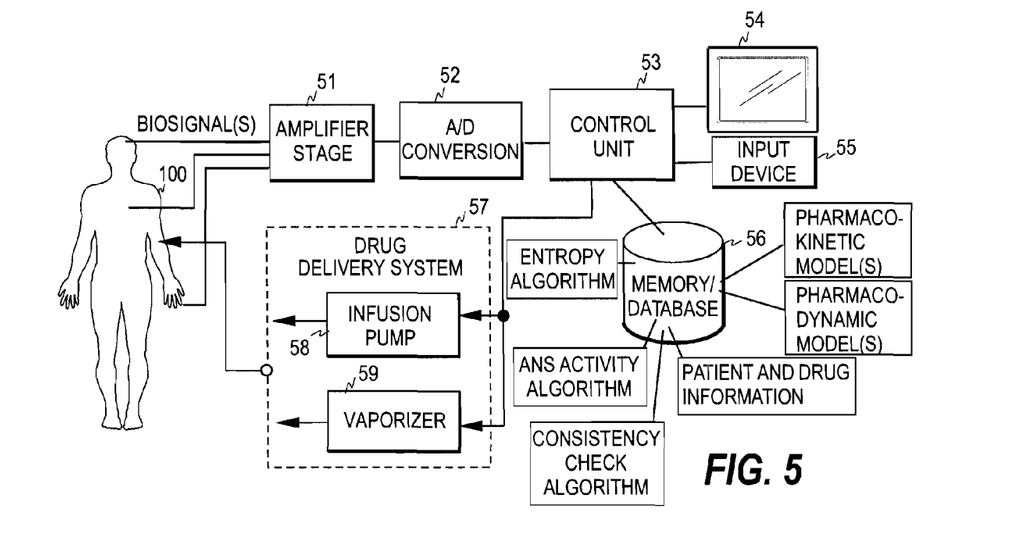
FIG. 5 illustrates one embodiment the system of the invention.

In the embodiment of FIG. 2, the consistency check involves checking whether either the hypnotic drug effect or the ANS activity is able to explain the behavior of the measure and thus shows consistent behavior with the measured value. However, since the embodiment of FIGS. 3 and 4 is based on a predicted value of the hypnotic level, a certain degree of consistency is required from both the drug effect information and the ANS state information, i.e. an anomaly is detected if changes in either the hypnotic drug effect or in the ANS activity, or in both, are inconsistent with the changes in the measured hypnotic level. In other words, the detection of an anomaly may be based on absence of consistency (FIG. 2) in both types of information or presence of inconsistency in either or both types of information (FIGS. 3 and 4). FIG. 5 illustrates one embodiment of the system or apparatus according to the invention. The physiological signals obtained from the sensors attached to a patient 100 are supplied to an amplifier stage 51, which amplifies the signals before they are sampled and converted into digitized format in an A/D converter 52. The digitized signals are supplied to a control unit 53. It is assumed here that the same control unit that performs the detection of an anomaly is also responsible for measuring the hypnotic level and the ANS activity, and for producing the drug effect information. However, the control unit may comprise one or more processor/computer units sharing the tasks. As discussed above, the hypnotic level is measured based on one or more EEG signals, while the ANS activity is typically measured based on PG or PPG and ECG signals.

Figure 6:
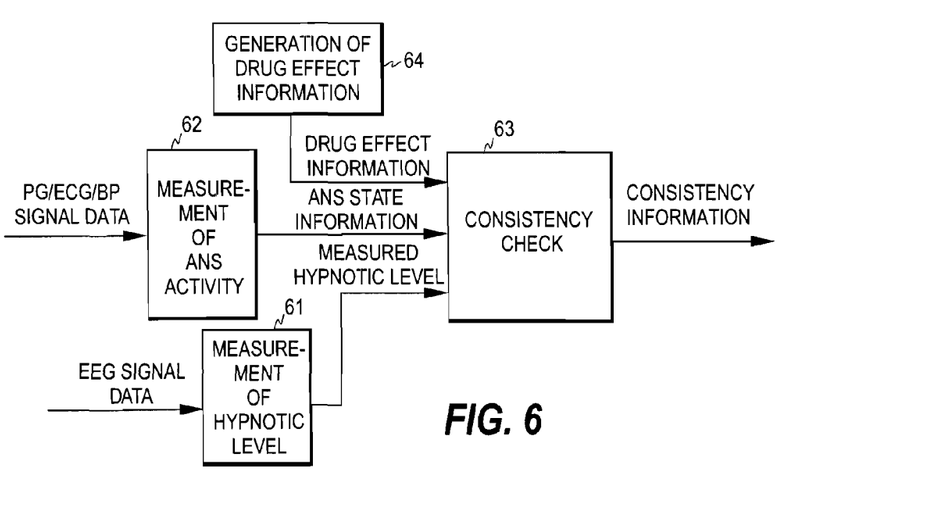
FIG. 6 illustrates the operational modules of the control unit of the system shown in FIG. 5.

The control unit is provided with a memory or database 56 holding the digitized signal data obtained from the sensors. As to the hypnotic level, the control unit may comprise the algorithm needed to calculate the measure indicative of the hypnotic level, such as an entropy algorithm. As to the ANS state information, the control unit may also store the relevant algorithms and produce the time series representing the ANS activity. As to the consistency check, the control unit may further include the algorithms for the consistency check including the rules/algorithms for taking appropriate actions if an anomaly is detected. As shown in FIG. 6, in this embodiment the control unit may thus include three or four operational modules or units: a first calculation unit 61 configured to derive a time series for a measure indicative of the hypnotic level, a second calculation unit 62 configured to form a time series representing the ANS state information, and a third calculation unit 63 configured to perform the consistency check and to produce consistency information at least when an anomaly is detected in the hypnotic level. A fourth unit 64 may produce the drug effect information, if the said information is not directly available.

With reference to FIG. 5 again, the system of the invention may further include a drug delivery system 57 which is controlled by the control unit. The drug delivery system typically comprises an anesthesia delivery unit, which may comprise an intravenous infusion pump 58 for intravenously administered drugs and/or a vaporizer 59 for inhaled drugs. The number and selection of the drugs available in the delivery unit may vary, and a practical and cost-effective implementation may include only one drug for each effect type. The drug delivery system may further include the pharmacokinetic and pharmacodynamic models for the drugs that may be administered through the drug delivery system. These models may be stored in the memory or database 56. As discussed above, the pharmacokinetic model typically provides the drug effect information required by the consistency check, since it indicates the brain concentration of the hypnotic drug administered to the subject.

The control unit receives the input information supplied by a user through a user input device 55, which may include a keyboard, a mouse, and/or a bar code reader, for example. The user interface of the system further comprises a monitor 54 for displaying various information to the user. The control unit may define the delivery rates of the drugs based on the input information and the models stored in the database.

The drug delivery system of FIG. 5 may be an open or closed loop drug administration system, i.e. the control unit may or may not utilize the hypnotic level measured and/or the state information determined for automatically controlling the administration of drugs.

In a closed loop drug administration system, the actions taken (steps 27 and 37) upon detection of an anomaly may depend on the hypnotic level. For example, if the hypnotic level does not indicate that the patient might soon regain consciousness, i.e. if the entropy levels obtained by the measurement and by the estimation are both still rather low, the system may simply freeze the administration of the hypnotic drug(s) to its current level and provide an indication of the situation to the user of the system. The indication may be transferred to a remote device to send for a clinician. If the hypnotic level indicates that there is no risk of an overdose, the system may slightly increase the amount of hypnotic drug administered to ascertain that the patient will not regain consciousness, and inform the user about the situation.

However, the actions upon detection of an inconsistent change may be restricted to the generation of an indication that alerts the user to the anomalous situation.

Instead of one or more processors in a centralized control unit, the processing of the data may also be distributed among different units/processors (servers) within a network, such as a hospital LAN (local area network). The apparatus of the invention may thus also be implemented as a distributed system.

A measurement device determining the hypnotic level and the ANS activity may also be upgraded to a device capable of indicating the consistency of the hypnotic index with the other information components. Such an upgrade may be implemented by delivering to the measurement device a software module that enables the device to carry out the consistency check. The software module may be delivered, for example, on a data carrier, such as a CD or a memory card, or through a telecommunications network. The software module may be provided with access to the data memory of the device so that it can retrieve the data necessary for performing the consistency check. The content of the software module may depend on the capabilities of the measurement device; if the measurement device is capable of producing measures for both the hypnotic level and the ANS activity, the software module includes only a program code portion configured to perform the consistency check based on the measure and to alert the user when an anomaly is found. However, if the measurement device lacks, for example, the ability to determine a measure indicative of ANS activity, but stores data from which such a measure may be derived, the software module may further include a portion configured to derive the measure based on the said data.

Although the invention was described above with reference to the examples shown in the appended drawings, it is obvious that the invention is not limited to these, but may be modified by those skilled in the art without departing from the scope and spirit of the invention.

I claim:

1. A method for detecting an anomaly in a measurement of the hypnotic level of a subject, the method comprising:
   monitoring using a patient monitor a change in a measure indicative of the hypnotic level in the subject;
   receiving at a processing unit state information indicative of the activity of the autonomous nervous system of the subject;
   receiving at the processing unit drug effect information indicative of the hypnotic drug effect in the subject;
   comparing the change in the measure to one of the drug effect information and the state information;
   checking with the processing unit whether the change in the measure is a consistent change with at least one of the drug effect information and the state information; and
   detecting with the processing unit an anomaly, wherein an anomaly is indicative that the change in the measure is not a consistent change with at least one of the drug effect information and the state information, and wherein the anomaly is indicative of an alteration in the normal relation between the measure and the at least one of the drug effect information and the state information.

2. A method according to claim 1, wherein the checking includes:
   defining an estimate for the measure based on a model that depends on the state information and on the drug effect information; and
   determining a variable indicative of the difference of the measure and the estimate;
   wherein the detecting includes detecting the anomaly when the variable fails to remain within a predetermined value range.

3. A method according to claim 1, wherein:
   the checking includes checking whether the change in the measure is a consistent change with changes in the drug effect information and the state information; and
   the detecting includes detecting the anomaly when the checking indicates that the change in the measure is not a consistent change with both the drug effect information and the state information.

4. A method according to claim 1, further comprising:
   deriving a rate of change in the measure; and
   comparing the rate of change to a predetermined threshold value.

5. A method according to claim 4, wherein the comparing indicates that the rate of change exceeds the predetermined threshold value and then the checking is triggered.

6. A method according to claim 5, wherein the checking is aborted if it is detected that the change in the measure is a consistent change with one of the drug effect information and the state information.

7. A method according to claim 1, further comprising:
   administering a hypnotic drug to the subject; and
   controlling the administering in response to the detecting.

8. A method according to claim 7, wherein the controlling includes freezing the administering to its current state.

9. A method according to claim 1, further comprising generating, in response to the detecting, an indication informing a user about the anomaly.

10. A method according to claim 1, further comprising deriving the measure from EEG signal data obtained from the subject.

11. A method according to claim 1, further comprising deriving the state information from plethysmographic and ECG signal data obtained from the subject.

12. An apparatus for detecting an anomaly in a measurement of the hypnotic level of a subject, the apparatus comprising:
   a monitoring unit configured to monitor a measure indicative of the hypnotic level in the subject;
   a first interface unit configured to receive state information indicative of the activity of the autonomous nervous system of the subject;
   a second interface unit configured to receive drug effect information indicative of the hypnotic drug effect in the subject; and
   a calculation unit configured to:
      perform a consistency check based on the drug effect information and the state information, thereby to check whether the measure fulfills a predetermined consistency condition requiring that any change in the measure is a consistent change with at least one of the drug effect information and the state information; and
      detect an anomaly, wherein an anomaly is indicative that the measure fails to fulfill the predetermined consistency condition, wherein the anomaly is indicative of an alteration in the normal relation between the measure and at least one of the drug effect information and the state information.

13. An apparatus according to claim 12, wherein the monitoring unit obtains EEG signal data from the subject and wherein the measure is indicative of an entropy of the EEG signal data.

14. An apparatus according to claim 12, wherein the calculation unit is configured to:
   define an estimate for the measure based on a model that depends on the state information and on the drug effect information;
   determine a variable indicative of the difference of the measure and the estimate; and
   detect the anomaly when the variable fails to remain within a predetermined value range.

15. An apparatus according to claim 12, wherein the calculation unit is configured to:
   check whether changes in the measure are a consistent change with changes in the drug effect information and the state information; and
   detect the anomaly when the checking indicates that the changes in the measure are not a consistent change with both the drug effect information and the state information.

16. An apparatus according to claim 15, wherein the calculation unit is further configured to:
   derive a rate of change in the measure;
   compare the rate of change to a predetermined threshold value, indicating that the rate of change exceeds the predetermined threshold value and then perform the consistency check.

17. An apparatus according to claim 12, further comprising a drug delivery unit configured to administer at least a hypnotic drug to the subject.

18. An apparatus according to claim 17, further comprising a non-transitory computer-readable medium operatively connected to the second interface unit and encoded with instructions executable to provide a pharmacokinetic model.

19. An apparatus according to claim 12, further comprising an indicator unit configured to give an indication of the anomaly.

20. An apparatus for detecting anomaly in a measurement of the hypnotic level of a subject, the apparatus comprising:
   monitoring means for monitoring a measure indicative of the hypnotic level in the subject;
   first reception means for receiving state information indicative of the activity of the autonomous nervous system of the subject;
   second reception means for receiving drug effect information indicative of the hypnotic drug effect in the subject; and
   calculation means for performing a consistency check based on the drug effect information and the state information, the calculation means being configured (i) to detect a change in the measure, (ii) to check whether the measure fulfills a predetermined consistency condition requiring that the change in the measure is a consistent change with at least one of the drug effect information and the state information, and (iii) to detect an anomaly, wherein an anomaly is indicative that the measure fails to fulfill the predetermined consistency condition, and wherein the anomaly is indicative of an alteration in the normal relation between the measure and at least one of the drug effect information and the state information.

21. A non-transitory computer-readable medium encoded with a computer program product comprising:
   instructions executable to compare a change in a measure indicative of the hypnotic level in the subject to drug effect information indicative of hypnotic drug effect in the subject and state information indicative of the activity of the autonomous nervous system of the subject;
   instructions executable to determine whether the measure fulfills a predetermined consistency condition requiring that the change in the measure is a consistent change with at least one of the drug effect information and the state information; and
   instructions executable to detect an anomaly, wherein an anomaly is indicative that the measure fails to fulfill the predetermined consistency condition, wherein the anomaly is indicative of an alteration in the normal relation between the measure and at least one of the drug effect information and the state information.

22. The non-transitory computer-readable medium of claim 21, further comprising instructions executable to derive the measure from EEG signal data obtained from the subject.

23. The non-transitory computer-readable medium of claim 22, further comprising instructions executable to derive the state information from plethysmographic and ECG signal data obtained from the subject.

* * * * *